(12) United States Patent
Sakaguchi et al.

(10) Patent No.: US 9,987,172 B2
(45) Date of Patent: Jun. 5, 2018

(54) DISPOSABLE DIAPER WITH COMPRESSED UNITS

(71) Applicant: UNICHARM CORPORATION, Ehime (JP)

(72) Inventors: Satoru Sakaguchi, Kanonji (JP); Kana Sawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 861 days.

(21) Appl. No.: 14/386,717

(22) PCT Filed: Mar. 28, 2013

(86) PCT No.: PCT/JP2013/059257
§ 371 (c)(1),
(2) Date: Sep. 19, 2014

(87) PCT Pub. No.: WO2013/147021
PCT Pub. Date: Oct. 3, 2013

(65) Prior Publication Data
US 2015/0051568 A1    Feb. 19, 2015

(30) Foreign Application Priority Data
Mar. 30, 2012    (JP) .................................. 2012-082909

(51) Int. Cl.
*A61F 13/15*    (2006.01)
*A61F 13/20*    (2006.01)
(Continued)

(52) U.S. Cl.
CPC .. *A61F 13/49017* (2013.01); *A61F 13/49001* (2013.01); *A61F 13/49406* (2013.01);
(Continued)

(58) Field of Classification Search
CPC .......... A61F 13/49001; A61F 13/49017; A61F 13/49406; A61F 13/49413; A61F 13/533; A61F 2013/49088
See application file for complete search history.

(56) References Cited

U.S. PATENT DOCUMENTS 5,662,636 A * 9/1997 Benjamin ......... A61F 13/49009
604/385.28
6,926,702 B1 * 8/2005 Wilkinson ............... A61F 13/49
604/385.01
(Continued)

FOREIGN PATENT DOCUMENTS

AU    2013218941 A1    9/2014
EP    2813198 A1    12/2014
(Continued)

OTHER PUBLICATIONS

Office Action in GCC Patent Application No. 2013-23989, dated Sep. 19, 2016.
(Continued)

*Primary Examiner* — Michele M Kidwell
(74) *Attorney, Agent, or Firm* — Hauptman Ham, LLP (57) ABSTRACT

An absorber of a disposable diaper includes a first region extending from an end at the side of the rear waistline region of the absorber towards a side of the crotch region, and a second region arranged adjacent to the first region at the side of the crotch region from the first region, and having a lower bending rigidity than the first region. The end at the side of the rear waistline region of the leg stretch unit and the end at the side of the rear waistline region of the contracted unit in the leg side stretch unit are arranged at the side of the crotch region from the end at the side of the rear waistline region of the first region, and are also arranged at the side of
(Continued)

the rear waistline region from the end at the side of the crotch region of the first region.

14 Claims, 7 Drawing Sheets

(51) Int. Cl.
*A61F 13/49* (2006.01)
*A61F 13/494* (2006.01)
*A61F 13/533* (2006.01)

(52) U.S. Cl.
CPC ...... *A61F 13/49413* (2013.01); *A61F 13/533* (2013.01); *A61F 2013/15357* (2013.01); *A61F 2013/4948* (2013.01); *A61F 2013/49066* (2013.01); *A61F 2013/49088* (2013.01)

(56) References Cited

U.S. PATENT DOCUMENTS

2004/0002690 A1* 1/2004 Miyamoto ........ A61F 13/49017
 604/385.25
2015/0250657 A1* 9/2015 Sakaguchi ............ A61F 13/494
 604/385.16

FOREIGN PATENT DOCUMENTS

| JP | 2003-93442 A | 4/2003 |
| JP | 2004-57413 A | 2/2004 |
| JP | 2008-253289 A | 10/2008 |
| JP | 2009-207778 A | 9/2009 |

OTHER PUBLICATIONS

Office Action in AU Patent Application No. 2013241164, dated Nov. 1, 2016.
Office Action in EA Application No. 201401051, dated Aug. 4, 2016.
Office Action dated Jun. 2, 2015, corresponding to Chinese patent application No. 201380016649.6.
Notification of Reason for Rejection dated Feb. 12, 2013 in corresponding Japanese Application No. 2012-082909 filed Mar. 30, 2012.
International Search Report dated Jun. 18, 2013 in International Application No. PCT/JP2013/059257 filed Mar. 28, 2013.
Extended European Search Report dated Oct. 30, 2015, corresponding to European Patent Application No. 13768837.0.
Office Action in Egyptian Patent Application No. PCT1542/2014, dated May 16, 2017.

* cited by examiner

DISPOSABLE DIAPER WITH COMPRESSED UNITS

RELATED APPLICATIONS

The present application is a National Phase of International Application Number PCT/JP2013/059257, filed Mar. 28, 2013, which claims priority to Japanese Application Number 2012-082909, filed Mar. 30, 2012.

TECHNICAL FIELD

The present invention relates to a disposable diaper.

BACKGROUND ART

Conventionally, there is known a disposable diaper which has a front waistline region, a rear waistline region, a crotch region, a pair of leg hole openings, an absorber running across a crotch region and extending towards the front waistline region and rear waistline region, and a fastening tape provided in the rear waistline region. A disposable diaper thus configured can be easily worn by securing the fastening tape to the target portion of the front waistline region, and is therefore used widely for newborns, and infants and toddlers.

Furthermore, in such a disposable diaper provided with a fastening tape, in order to improve the fitting when the disposable diaper is worn, there is known a structure having a leg stretch unit provided along a leg hole opening arranged in the area around the legs of the wearer, and a leg side stretch unit provided to cover an outer end in the widthwise direction of an absorber (for example, see Patent Literature 1).

CITATION LIST

Patent Literature

[PTL 1]
Japanese Unexamined Patent Application Publication No. 2009-207778

SUMMARY OF INVENTION Summary of Invention

However, the above disposable diaper has the below problems.

When a new born, or an infant and toddler is made to wear a disposable diaper provided with a fastening tape, generally, the disposable diaper is put on by placing the hips of the wearer in the rear waistline region of the absorber with the disposable diaper in an expanded state in the product longitudinal direction.

However, the leg stretch unit and leg side stretch unit are configured to be stretchable in at least the product longitudinal direction, and in the state prior to wearing the diaper, wrinkles may occur in the region in which the end of the leg stretch unit and the leg side stretch unit in the product longitudinal direction is arranged, and also in a fixed range extending in the widthwise direction from this region. In this way, when wrinkles occur in the region in which the end of the leg stretch unit and the leg side stretch unit in the product longitudinal direction is arranged, it is not possible to arrange the hips at an appropriate position, thus causing the wearing position to deviate.

Thus, the present invention has been achieved in view of the above problem, and an object thereof is to provide a disposable diaper, with which it is possible to easily wear an open-type disposable diaper having a fastening tape at the correct position, and to prevent the deviation of the wearing position.

The disposable diaper (disposable diaper 10) according to the present disclosure is summarized as a disposable diaper including; a front waistline region (front waistline region 20); a rear waistline region (rear waistline region 30); a crotch region (crotch region 25) positioned between the front waistline region and the rear waistline region; an absorber (absorber 40) running across the crotch region and extending in the front waistline region and the rear waistline region; a pair of fastening tapes (fastening tapes 90) extending from the rear waistline region to the outer side in the product widthwise direction, and being secured to the front waistline region, a product longitudinal direction (product longitudinal direction L) from the front waistline region towards the rear waistline region; a product widthwise direction (product widthwise direction W) that is perpendicular to the product longitudinal direction; a pair of leg hole openings (leg hole openings 35) being formed; a leg stretch unit (leg stretch unit 75) arranged around the leg hole openings and can expand and contract along at least the product longitudinal direction; and an leg stretch unit stretch unit (leg stretch gather 80) arranged at the inner side in the product widthwise direction from the leg stretch unit, and having a contracted unit that can expand and contract along the product longitudinal direction, wherein the absorber includes a first region (first region 41) extending from an end at the side of the rear waistline region of the absorber towards a side of the crotch region, and a second region (second region 42) arranged adjacent to the first region at the side of the crotch region from the first region, and having a lower bending rigidity than the first region, and the end at the side of the rear waistline region of the leg stretch unit and the end at the side of the rear waistline region of the leg stretch unit and the end at the side of the rear waistline region of the contracted unit in the leg side stretch unit are arranged at the side of the crotch region from the end at the rear waistline region side of the first region, and are also arranged at the side of the rear waistline region from the end at the crotch region side of the first region.

DESCRIPTION OF EMBODIMENTS

Hereinafter, an embodiment of a disposable diaper according to the present invention is described with reference to accompanying drawings. In the following description of the drawings, the same or similar reference numerals are used to designate the same or similar portions. It will be appreciated that the drawings are schematically shown and the ratio and the like of each dimension are different from the real ones.

Therefore, a specific dimension should be determined in view of the following description. Moreover, among the drawings, the respective dimensional relations or ratios may differ.

(1) Overall Schematic Configuration of Disposable Diaper

Figure 1:
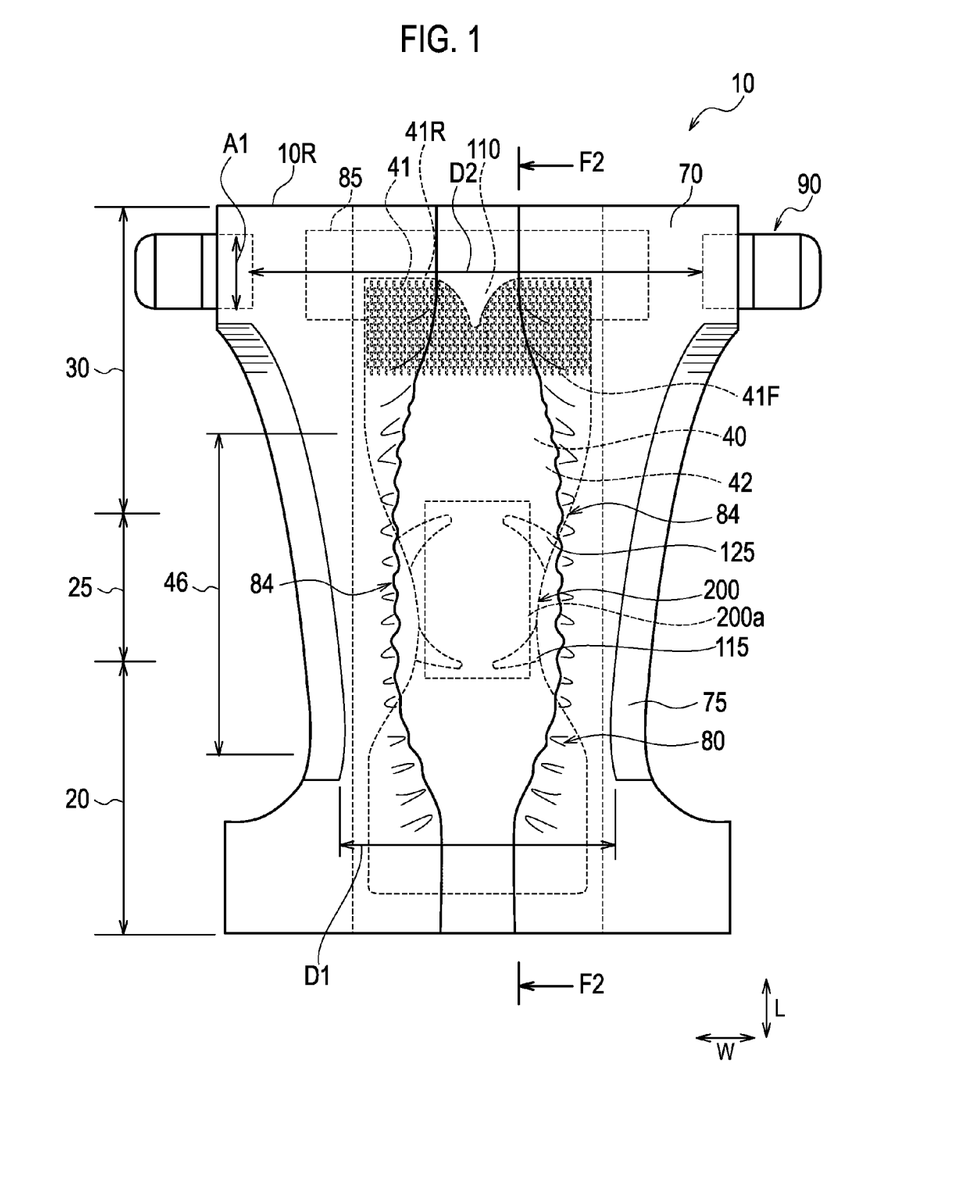
FIG. 1 is an exploded plan view of a disposable diaper according to the present embodiment.
Figure 2:
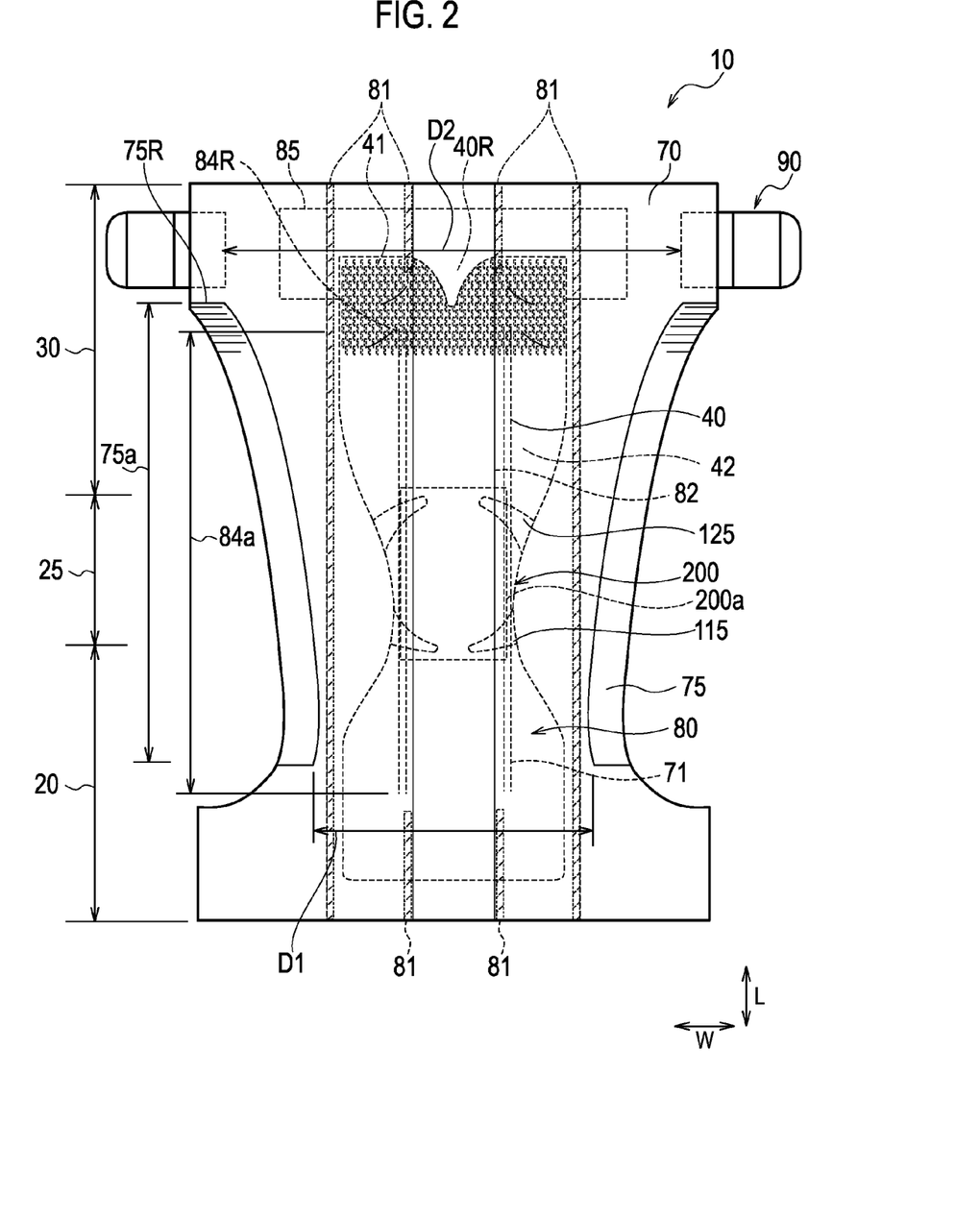
FIG. 2 is an exploded plan view of a disposable diaper according to the present embodiment.
Figure 3:
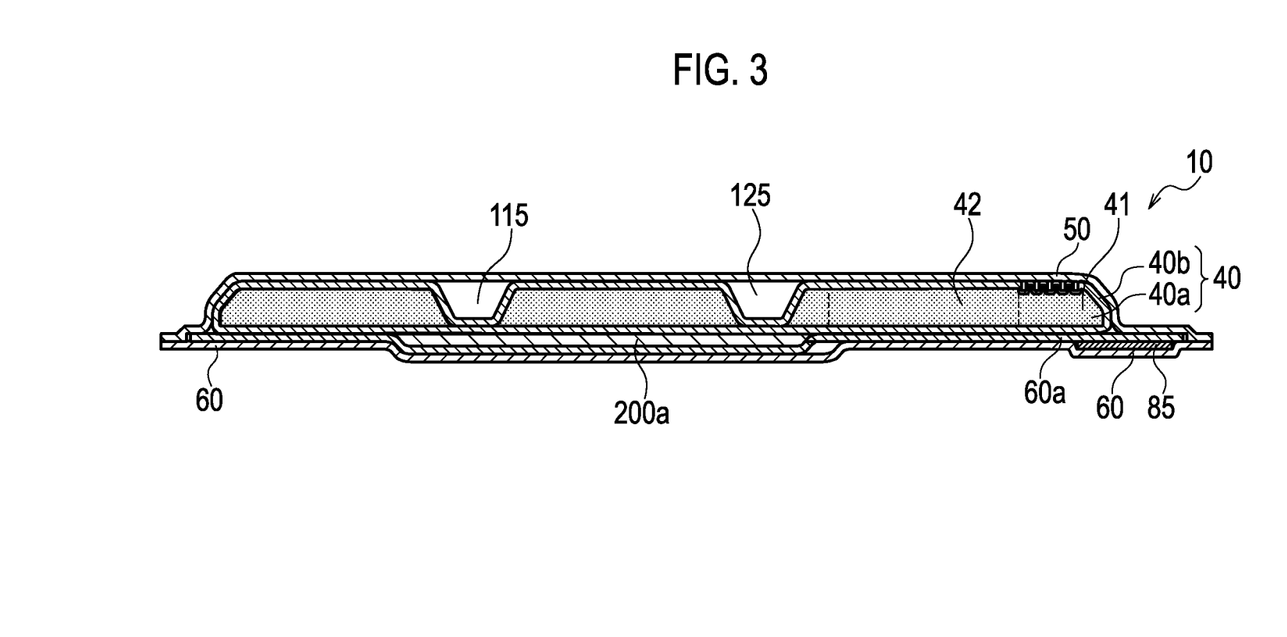
FIG. 3 is a cross-sectional view of the disposable diaper along an F2-F2 line shown in FIG. 1.

FIG. 1 and FIG. 2 are exploded plan views of a disposable diaper 10 according to the present embodiment. FIG. 3 is a cross-sectional view of the disposable diaper 10 along the F2-F2 line shown in FIG. 1. It should be noted that the exploded plan view of FIG. 1 is a diagram in which leg stretch units 75 and leg side gathers 80 are in an expanded state such that wrinkles are not formed in a topsheet 50 and side flaps 70, for example, that configure the disposable diaper 10, but for the sake of description, the leg side gathers 80 are illustrated in a contracted state.

The disposable diaper 10 includes a front waistline region 20, a crotch region 25, and a rear waistline e region 30. The front waistline region 20 is a portion that is in contact with the front waistline portion (abdominal portion) of the wearer. Furthermore, the rear waistline region 30 is a portion that is in contact with the rear waistline portion (back portion) of the wearer. The crotch region 25 is positioned between the front waistline region 20 and the rear waistline region 30. Furthermore, a pair of leg hole openings 35 are formed in the disposable diaper 10 (see FIG. 7). The leg hole openings 35, which are provided in the side ends in the widthwise direction of the disposable diaper, correspond to the portion arranged along the area around the legs of the wearer when the disposable diaper is worn by the wearer.

In the present embodiment, the direction from the front waistline portion 20 to the rear waistline portion 30 is called the product longitudinal direction L, and the direction perpendicular to the product longitudinal direction L is called the product widthwise direction W.

The disposable diaper 10 includes an absorber 40 running across the crotch region 25 and extending towards the front waistline region 20 and the rear waistline region 30. The absorber 40 includes an absorbent core 40a and a core wrap 40b.

The absorbent core 40a is the same as that in the conventional disposable diaper, and can be configured appropriately by using well-known components and materials, such as ground pulp and high absorbent polymer. The absorbent core 40a is wrapped by the sheet-like core wrap 40b. The core wrap 40b is a sheet for covering the absorbent core 40a. A part of at least the skin surface side of the core wrap 40b is configured by various nonwoven fabrics or a tissue sheet having permeability. For example, an air-through nonwoven fabric, a spunbond nonwoven fabric, or an SMS (spunbond-meltblown-spunbond) nonwoven fabric having a mass of approximately 10 to 30 g/m2, or a tissue sheet having a mass of approximately 10 to 30 g/m2 can be used.

On the top side (skin contact surface side) of the absorber 40 is provided a liquid-permeable topsheet 50. Furthermore, on the back side (non-skin contact surface side) of the absorber 40 is provided a liquid-impermeable backsheet 60a.

A side flap 70 is provided in each side edge in the product widthwise direction W of the absorber 40. The side flaps 70 are made of one or two or more layers of nonwoven fabrics overlapping one another. Furthermore, a fastening tape 90 is provided in each of the pair of side flaps 70.

The fastening tape 90 extends along the product widthwise direction W in the rear waistline region 30, and holds the disposable diaper 10 onto the body of the wearer by being secured to the non-skin contact surface side of the front waistline region 20.

In the present embodiment, the waistline retaining unit is configured by the front waistline region 20, the rear waistline region 30, and the fastening tape 90.

Furthermore, the disposable diaper 10 includes a crotch stretch unit 200a formed in the crotch region 25 and can expand and contract in the product longitudinal direction L. Specifically, the crotch stretch unit 200a is arranged in a crotch unit 200 formed in the crotch region 25. The configuration of the crotch unit 200 and the crotch stretch unit 200a is described later in detail.

The top side (topsheet 50 side) of the absorber 40 is formed around the leg hole openings 35, and includes a pair of leg stretch units 75 that can expand and contract in the product longitudinal direction L.

The leg stretch units 75 are configured to be longer than the crotch stretch unit 200a in the product longitudinal direction L, and are provided at the outer side from the crotch stretch unit 200a in the product widthwise direction W.

It must be noted that it is sufficient when the leg stretch units 75 are configured such the leg hole openings 35 is stretchable in the product longitudinal direction, and the leg stretch units may be arranged along the leg hole openings 35, or some of the leg stretch units may be arranged in an inclined state with respect to the leg hole openings 35. In FIG. 2, the contracted region 75a in the product longitudinal direction of the leg stretch unit 75 is illustrated.

Furthermore, the leg stretch units 75 correspond to the portion that is substantially contracted in the product longitudinal direction by a stretchable sheet or the like, and can be conceived as the portion exclusive of the portion in which the stretchable sheet is arranged in a state in which the contractile force is not exhibited.

The leg stretch units 75 of the present embodiment are configured by a stretchable sheet. For example, a stretch film formed by melting a thermoplastic elastomer resin, such as urethane and styrene, and then converting into the shape of a film, a stretchable nonwoven fabric formed from stretchable fibers, or a composite sheet formed by pasting together inextensible sheets that have been partially cut into a stretch film and stretchable nonwoven fabric, or have been made fragile can be used as the stretchable sheet.

Furthermore, instead of the stretchable sheet, a single or a plurality of thread-like or band-like elastic members made of polyurethane elastic fibers and natural rubber may be arranged to configure the leg stretch units 75.

It is preferred that the stretchable sheet configuring the leg stretch units 75 has, at least in the crotch region 25, a width of 5 mm (width in the product widthwise direction W in the natural state of the disposable diaper 10) or more and 45 mm or less, and more preferably 12.5 mm or more and 35 mm or less. When the width is less than 5 mm, the effect of lowering of the load on the skin by the elastic elements achieved by substantially running, in the form of a surface of the leg stretch units, along the area around the legs of the wearer so as to prevent the partial concentration of the securing force is not exhibited, and when the width exceeds 45 mm, the region along the area around the legs becomes too wide in comparison to the length in the product widthwise direction of the entire disposable diaper, and as a result, the stretchable sheet might become entangled at the side of the wearer's body, or may turn over.

The ratio of expansion and contraction of the leg stretch units 75 is preferably 1.6 times to 2.4 times. In the present embodiment, the ratio of expansion and contraction of the leg stretch units 75 is set to 2.0 times.

It is to be noted that a ratio of expansion and contraction means degree of expansion and contraction of the leg stretching unit 75 in an expansion and contraction direction (the product longitudinal direction L in the present embodiment) and is determined as follows.

The ratio of expansion and contraction of the leg gathers 75=(Length of the leg gathers 75 during maximum extension)/(Length of the leg gathers 75 in the natural state)

If the disposable diaper 10 is inserted in a package, take the diaper out of the package, and use a sample that has been kept in such a condition for 12 hours in an ambient temperature of 20° C.±2° C., and a relative humidity of 60%±5% RH.

Next, use a spring measure (tape: covered with glass fiber reinforced vinyl chloride) manufactured by Shinwa Rules Co., Ltd., keep it along the area to be measured, and measure the length of the disposable diaper 10 in this state, that is, the length of the leg gathers 75 when the disposable diaper 10 is in the natural state, and the length of the leg gathers 75 when the disposable diaper 10 is extended from its natural state until wrinkles caused by the elastic members are not visible to the naked eye. The above measurement was performed for 10 samples, and the average value was assumed as the aforementioned length.

Hereinafter, the measurement of the "length" described in the specification will be performed based on the aforementioned measuring method.

Furthermore, the gap between the inner ends of the pair of the left-right leg stretch units 75 in the product widthwise direction W widens from the crotch region 25 towards the front waistline region 20, and also widens from the crotch region 25 towards the rear waistline region 30. By arranging the leg stretch units in a shape that is narrow in the crotch portion and widens towards the front and rear waistline s, the leg stretch units can run along the line of the body because of which the leg stretch units are expanded and arranged appropriately in the area around the legs of the wearer.

Additionally, the gap (D1 in the figure) between the ends of the front waistline region 20 of the pair of left-right leg stretch units 75 is narrower than the gap (D2 in the figure) between the ends of the rear waistline region 30 of the pair of left-right leg stretch units 75. The gap is the distance between the inner ends of the pair of left-right leg stretch units 75 in the product widthwise direction W that is measured after expanding and holding the disposable diaper 10 from the natural state to the state when no wrinkles are formed, in the product longitudinal direction L and the product widthwise direction W.

The extension of the skin surface of the body of the wearer is particularly large in the hip, and is remarkable at a position towards the outer widthwise direction. Furthermore, the leg stretch units 75 are in contact with the body of the wearer. Because D2>D1, even when the movement of the wearer is added to the disposable diaper 10, the leg stretch units 75 in the hip can extend while being in contact with the body, and even when the amount of change in the extension is large, the leg stretch units 75 do not become stiff. Therefore, the shifting of the disposable diaper 10 can be controlled by the leg stretch units 75.

Additionally, in the inner side of the pair of leg stretch units 75 (closer to the center in the product widthwise direction W), a pair of leg side gathers (leg side stretch units) 80 extending along the product lengthwise direction L are provided. The leg side gathers 80, which are provided in the inner ends in the product widthwise direction of the side flaps, are upright stretchable gathers arranged on the inner side in the product widthwise direction from the leg stretch unit. The side flaps are folded back to the side of the topsheet in the inner ends in the product widthwise direction and are formed by laminating two layers. Elastic members 76 (see FIG. 2) are provided between the two-layered side flaps in an expanded state in the longitudinal direction. The leg side gathers 80 are formed by the side flaps 70 and the elastic members 76.

The exploded plan view of the disposable diaper illustrated in FIG. 1 is the state in which the elastic member 71 of the leg side gathers 80 is contracted, and the exploded plan view of the disposable diaper illustrated in FIG. 2 is the state in which the elastic member 71 of the leg side gathers 80 is expanded. In the natural state, the disposable diaper is in the state illustrated in FIG. 1.

The leg side gathers 80 have the backsheet 60a, a joining portion 81 joined either with an exterior sheet 60 or the topsheet 50, and a free end portion 82 positioned on the opposite side of the joining portion 81 and provided with elastic members. As for the leg side gathers 80, when the diaper is worn, the joining portion 81 rises up as the proximal end and a contracted unit 84 of the free end portion 82 is in contact with the skin of the wearer as the apex.

The contracted unit 84 is the portion that is substantially contracted in the product longitudinal direction by the elastic member 71, and can be conceived as the portion exclusive of the portion in which the elastic member 71 is arranged in a state in which the contractile force is not exhibited. Furthermore, in FIG. 2, in the leg side gathers, the joining portion 81 where the side flaps 70 and the topsheet 50 are joined is illustrated by adding slanted lines, and the region 84a in the product longitudinal direction of the contracted unit 84 is illustrated.

A plurality of joining portions 81 are provided, and while some joining portions 81 are arranged at the outer side in the product longitudinal direction from the contracted unit 84, the other joining portions are arranged at the outer side in the product widthwise direction from the contracted unit 84. Thus, the leg side gathers 80 are configured such that rather than the entire length of the free end portion 82 rising up at the side of the wearer, the central portion in the product longitudinal direction including the crotch region 25 rises up at the side of the wearer.

Of the joining portions 81 of the leg side gathers 80, the joining portions that are arranged at the outer side in the product widthwise direction from the contracted unit 84 are arranged between the crotch stretch unit 200a and the leg stretch unit 75, in the product widthwise direction W. The joining portions that are arranged at the outer side in the product widthwise direction from the contracted unit 84 are joined with the backsheet 60a.

Of the joining portions 81 of the leg side gathers 80, the joining portions that are arranged at the outer side in the product longitudinal direction from the contracted unit 84 are joined with the topsheet 50. It must be noted that if the length in the product longitudinal direction of the topsheet 50 is shorter than the length in the product longitudinal direction of the entire disposable diaper, the joining portions that are arranged at the outer side in the product longitudinal direction from the contracted unit 84 may be joined with the exterior sheet 60 and the backsheet 60a.

Various types of configurations can be adopted for the joining portions 81 of the leg side gathers 80. The joining portions, for example, extend in the product longitudinal direction from the crotch to the front waistline region and the rear waistline region, and could be the portion joined with the topsheet or the portion joined with the liquid-impermeable backsheet and the exterior sheet at the outer side in the widthwise direction from the absorbent core 40a, and are configured to form an upright proximal end.

Furthermore, the leg side gathers are not limited to the above configuration as long as the leg side gathers are upright gathers arranged on the inner side in the product widthwise direction from the leg stretch unit, and any configuration of the leg side gathers that is well-known in the conventional art can surely be adopted.

It must be noted that the backsheet 60a is arranged between the absorber 40 and the exterior sheet 60, and functions as a leakage-preventing sheet.

Furthermore, a lower-back stretch unit 85 that can expand and contract in the product widthwise direction is provided between a pair of fastening tapes in the product widthwise direction. In the plan view, the lower-back stretch unit 85 is arranged between the pair of fastening tapes, and contracts the space between the fastening tapes in the widthwise direction. The lower-back stretch unit 85 is arranged at the skin contact surface side of the topsheet and contracts the space between the fastening tapes in the widthwise direction.

The member configuring the lower-back stretch unit 85 is not particularly restricted, but a member that is as thin as possible with a low rigidity, and has a small reduction in width, for example, a stretch film, is preferably used.

After being extended up to 1.5 to 2.5 times the length in the non-expanded state (natural state), the lower-back stretch unit 85 is adhered onto the exterior sheet 60 with a hot-melt adhesive or heat processing.

In the present embodiment, the lower-back stretch unit 85 is arranged between the exterior sheet 60 and the back sheet 60a (see FIG. 3). However, if the core wrap 40b is configured to extend in the outer side in the product longitudinal direction from the absorbent core 40a, the lower-back stretch unit 85 may be arranged between the core wrap 40b and the backsheet 60a or exterior sheet 60. The position of the lower-back stretch unit is not particularly restricted, but preferably, the lower-back stretch unit is arranged at the non-skin contact surface side from the absorber 40. Furthermore, in a region in which the absorber is not arranged, the lower-back stretch unit may be arranged between the side flaps 70 and the backsheet 60a or exterior sheet 60.

The lower-back stretch unit according to the present embodiment is configured to stretch in the product widthwise direction, however, the lower-back stretch unit may be configured to stretch in the product widthwise direction and the product longitudinal direction.

(2) Shape of Crotch Unit

Next, the shape of the crotch unit 200 will be described. As described above, the crotch unit 200 includes the crotch stretch unit 200a. The crotch stretch unit 200a is configured to be easily maintained in a flat shape as compared to the other portions of the absorber 40 when the disposable diaper is worn. The crotch unit 200 includes the crotch stretch unit 200a that can expand and contract in at least the product longitudinal direction L or the product widthwise direction W.

The crotch stretch unit 200a is provided separately and independently of the leg stretch unit 75, and is configured to contract 60% or more of the length in the widthwise direction of the absorbent core 40a in the position where the crotch stretch unit overlaps the absorbent core 40a (in the present embodiment, it is the position between the core wrap 40b that wraps the absorbent core 40a and the backsheet 60a). In this way, due to the contraction of the portion in which the absorbent core 40a is arranged by the crotch stretch unit 200a, the absorbent core 40a is constricted, and a flat shape is easily maintained as compared to the portion where the absorbent core 40a is not constricted.

On the other hand, the absorbent core 40a positioned in the front waistline region and the rear waistline region positioned on the outer side in the product longitudinal direction from the crotch stretch unit 200a is not contracted by the crotch stretch unit 200a, because of which the crotch unit 200 is arranged appropriately along the body without the entire absorber coming in excessively close contact with the body.

Furthermore, because the crotch unit 200 can be stretched along the product longitudinal direction L, the front waistline region 20 and the rear waistline region 30 rise up easily due to the contraction of the crotch unit 200, when the disposable diaper is worn, a flat crotch region is formed along the body at the crotch of the wearer. Because the front waistline region and the rear waistline region rise up from the crotch stretch unit 200a, the fitting of the disposable diaper 10 on the wearer improves. The crotch stretch unit 200a is preferably configured by a stretchable sheet. By configuring the crotch stretch unit 200a by a stretchable sheet, the absorbent core 40a of the region in which the stretchable sheet is arranged is constricted uniformly, and maintaining a flat shape becomes easier. It must be noted that the stretchable sheet, for example, can be configured by the same stretchable sheet as the leg stretch unit 75.

Furthermore, rather than the stretchable sheet, the crotch stretch unit 200a can also be configured by arranging a plurality of thread-like or band-like elastic members made from polyurethane elastic fibers and natural rubber. In this case, in order to uniformly constrict the absorbent core 40a by the crotch stretch unit 200a, the gap between the elastic members is preferably 7 mm or less, and more preferably 5 mm or less. Furthermore, in order to uniformly constrict the absorbent core 40a, the difference in the gap between adjacent elastic members is desired to be 0.5 mm or less.

Furthermore, the ratio of expansion and contraction of the crotch stretch unit 200a is preferably 1.2 times or more and 1.8 times or less, specifically. In the present embodiment, the ratio of expansion and contraction of the crotch stretch unit 200a is set to 1.4 times.

The ratio of expansion and contraction of the crotch stretch unit 200a implies the extent of the expansion and contraction of the crotch stretch unit 200a in the direction of expansion and contraction (product longitudinal direction L), and is stipulated as below:

The ratio of expansion and contraction of crotch stretch unit 200a=(Length of the crotch unit during maximum extension)/(Length of the crotch unit in the natural state) It should be noted that the ratio of expansion and contraction as used herein is to be measured as described below, for example.

Firstly, in a case where the disposable diaper 10 is inserted in a package, for example, then the disposable diaper 10 is taken out of the package, and the diaper is kept in such a condition for 60 minutes in an ambient atmosphere having a temperature of 20° C.±2° C., and a relative humidity of 60%±5% RH, and then a length of the crotch stretch unit is measured in the direction of expansion and contraction. This length is set to a "length in the direction of expansion and contraction of the crotch stretch unit 200a in the natural state".

Secondly, measurement is performed with respect to the length in the direction of expansion and contraction of the desired region in this state (that is, in the natural state), and the length in the direction of expansion and contraction of the desired region when the disposable diaper is extended from its natural state to a state in which wrinkles caused by the elastic members cannot be visually confirmed. This length is set to a "length in the direction of expansion and contraction of the crotch stretch unit 200a in the maximum extended state".

By thus setting the ratio of expansion and contraction of the crotch stretch unit 200a between 1.2 times and 1.8 times, it is possible to favorably follow the stretching of the skin of the wearer.

For example, when the wearer bends forward such that the front side of the body constricts, there exists a part in the skin at the side of the hip portion of the wearer that stretches by approximately 30% as compared to the state when the body has been stretched out.

That is, when the ratio of expansion and contraction of the crotch stretch unit 200a is 1.2 times or less, the contraction of the crotch stretch unit 200a in the natural state of the disposable diaper is insufficient, and as compared to the case when the crotch stretch unit 200a has not been provided, the difference in the ease of curving of the disposable diaper 10 is small because of which the front waistline region 20 does not rise at the desired position.

On the other hand, when the ratio of expansion and contraction of the crotch stretch unit 200a is more than 1.8 times, the contraction size in the contracting direction of the crotch stretch unit 200a becomes too large, because of which the region where the crotch stretch unit 200a exists easily comes in close contact with the body of the wearer rather than running along it, and the disposable diaper 10 easily shifts to the lower side of the wearer.

Furthermore, the center of the crotch stretch unit 200a in the product longitudinal direction L is arranged at the side of the front waistline region 20 from the center of the disposable diaper 10 in the product longitudinal direction L. However, the crotch stretch unit 200a is arranged to run across the center of the disposable diaper 10 in the product longitudinal direction L.

In such a case, in view of the rigidity of the absorber core 40a and the rigidity of other members configuring the disposable diaper 10, the thickness of the elastic members and the arrangement pitch can be selected appropriately, however, when the main body of the disposable diaper 10 is in the natural state (unextended state), the entire side edge in the product widthwise direction W of the absorber core 40a is preferable to be in a contracted state.

Furthermore, a notch 115 (notch 125) is formed in the crotch region 25 of the absorber 40. The notch 115 and the notch 125 is a region in which the absorbent core 40a configuring the absorber 40 does not exist. In the present embodiment, the notch 115 and the notch 125 correspond to a low rigidity unit in which the basis weight of the absorbent core 40a is lower than that of the other portion of the absorbent core 40a. It should be noted that instead of forming the notch 115 and the notch 125, the region of the notch 115 and the notch 125 may be such that the basis weight of the absorbent core 40a is lower than that of the other portion of the absorbent core 40a.

The notch 115 and the notch 125 exist along the edges in the product longitudinal direction L of the crotch unit 200. It should be noted that even though the notch 115 and the notch 125 are formed, the absorbent core 40a positioned in the front waistline region 20 and the rear waistline region 30, and the absorbent core 40a positioned in the crotch region 25 are preferred to be in continuation, particularly in the widthwise direction, rather than being completely separate.

As the notch 115 and the notch 125 run towards the outer side in the product widthwise direction W, the length in the product longitudinal direction L keeps on widening. As a result of such a shape, the outer side in the product widthwise direction W of the absorbent core 40a is constricted more easily, and a flat "bottom unit" is formed more easily. Furthermore, the absorbent core 40a positioned towards the front waistline region 20 from the notch 115, and the absorbent core 40a positioned towards the rear waistline region 30 from the notch 125 rise up from the "bottom unit", and can easily curve along the roundness of the body of the wearer (the abdominal portion and the hip), because of which the shape of the disposable diaper can be brought closer to the body of the wearer.

Furthermore, the edge towards the front waistline region 20 (rear waistline region 30) of the notch 115 (notch 125) is arc shaped. The shape of the edge of the notch 115 (notch 125) is such that the center of the arc is positioned in the rear waistline region 30 (front waistline region 20) from the edge. As a result of such a shape, the deformation along the roundness of the body of the wearer occurs more easily and remarkably.

(3) Shape of Absorber

Figure 4:
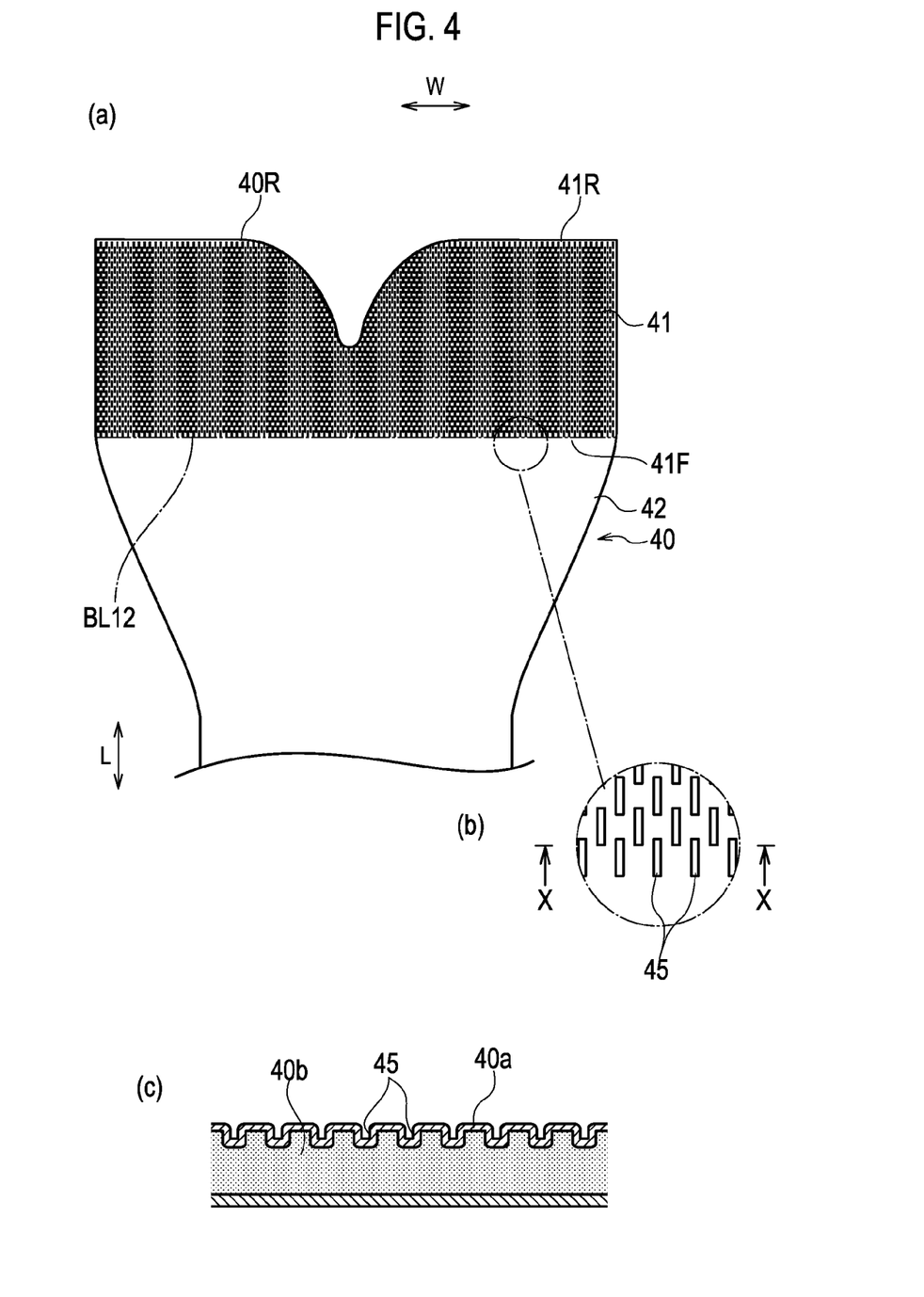
FIG. 4 is a diagram illustrating an absorber according to the present embodiment.

Next, the shape of the absorber 40 will be described. FIG. 4 is a diagram illustrating an absorber. FIG. 4(a) is an enlarged plan view as seen from the topsheet 50 side, FIG. 4(b) is a partial enlarged view of FIG. 4(a), and FIG. 4(c) is a view of the X-X cross-section of FIG. 4(b).

The absorber 40 includes a first region 41 extending from an end 40R at the side of the rear waistline region of the absorber towards the side of the crotch region, and a second region 42 arranged adjacent to the first region 41 at the side of the crotch region from the first region 41, and having a lower bending rigidity than the first region 41. The second region 42 is arranged at the side of the rear waistline region from the crotch stretch unit 200a and the notch 125.

The first region 41 is provided in the entire absorber in the product widthwise direction. In the first region 41, a compressed unit 45 in which the absorber 40 is compressed in the product thickness direction is formed. A plurality of the compressed units 45 are formed intermittently across the entire first region. On the other hand, the compressed units 45 are not formed in the second region 42. Thus, the bending rigidity of the first region 41 is configured to be higher than the bending rigidity of the second region 42.

The bending rigidity in the present embodiment is based on the rigidity value conforming to the Taber method (JISP8125), and can also be checked by measuring as described below. First of all, with the disposable diaper in the expanded state, a sample of the portion where the bending rigidity is to be measured (for example, the absorber) is extracted. As regards the sample, the portion to be measured is prepared with the dimensions of 70 mm sample length×38 mm in the widthwise direction perpendicular to the sample length direction, along the product widthwise direction or the product longitudinal direction. If a stretchable elastic member is included in the sample, the elastic member is removed. The Taber Stiffness Tester manufactured by Yasuda Seiki Seisakusho Ltd. is used for measuring the rigidity value. 10 samples are taken and measurement is performed for each sample, and the average value is set as the rigidity value.

The measurement procedure is as described in (a) through (e) below.

(a) Measure the thickness (A) of the extracted samples.

(b) Next, insert the sample such that the sample is in contact with the center of the chuck (lower) of the tester.

(c) Adjust the total left-right gap between the support roller and the sample to (A×0.80 (mm).

(d) Appropriately select an auxiliary weight such that the specified load scale is in the range of 15 to 85% of the maximum scale.

(e) Rotate the samples in both left and right directions, stop at the point where the 15° support marked line and the central marking of the pendulum match, and read the value on the tester. Consider the value on the left side of the scale as (B) and the value on the right side of the scale as (C).

The rigidity value is calculated by the below formula:

Rigidity value (mN·m)=(((B)+(C))/2)×(Auxiliary weight coefficient)×9.81×10−2     Formula If a width of 38 mm cannot be acquired for the specimen, perform conversion to the bending moment of 38-mm width.

The higher the rigidity value thus measured, the higher the bending rigidity, and the lower the rigidity value, the lower the bending rigidity.

The plurality of compressed units 45 are arranged in a staggered manner, and are configured such that the length in the product longitudinal direction is more than the length in the product widthwise direction. Thus, because the compressed units 45 are arranged discontinuously in a staggered manner, compressed portions and uncompressed portions co-exist in the first region 41. The uncompressed portions have a lower bending rigidity than the compressed portions and can be deformed flexibly, because of which the bending rigidity of the first region 41 can be increased, and the first region 41 can be arranged along the line of the body having a roundness.

It must be noted that when the absorbent core 40a has been wrapped by the core wrap 40b, the compressed units 45 may be compressed and formed in the thickness direction from the outer side of the core wrap 40b, or when the absorbent material configuring the absorbent core 40a is laminated, the basis weight of the absorbent material of the first region 41 may be set higher than that of the absorbent material of the second region 42, and the compressed units may be formed by compressing the absorbent core 40a in the thickness direction.

The absorber according to the present embodiment has been configured such that the bending rigidity in the first region 41 is higher due to the formation of the compressing units 45, however, the bending rigidity in the first region 41 may be configured to be higher than that in the second region 42 based on some other configuration as well.

In the absorber 40 of the rear waistline region, a notch 110 is provided as a low rigidity region that either has a basis weight lower than the other parts of the absorber, or where the absorbent core 40a does not exist. The notch 110 has a shape such that the length in the product widthwise direction shortens gradually from the center in the product widthwise direction of the end at the side of the rear waistline region of the absorber 40 towards the side of the crotch region. More specifically, the notch 110 has a wedge shape in the plan view of the disposable diaper. Furthermore, the boundary between the absorbent core 40a and the notch 110 is formed in the shape of an arc such as a convex shape towards the center in the product widthwise direction W. The absorber 40 at the outer side in the product widthwise direction from the notch 110 has a trapezoidal shape such as a convex shape towards the end of the side of the rear waistline region.

A part of the notch 110 is arranged with overlapping the lower-back stretch unit 85 in the plan view of the disposable diaper. It must be noted that in the present embodiment, the lower-back stretch unit 85 is arranged with overlapping a part of the notch 110, however, the notch 110 may be arranged with overlapping the entire lower-back stretch unit 85.

By forming such a notch 10, without obstructing the stretching of the lower-back stretch unit 85, even when the lower-back stretch unit 85 contracts, the notch 110 narrows and the space between the absorbers at both sides in the product widthwise direction from the notch 110 also narrows, because of which it becomes difficult for the absorber 40 to rise in the intended shape. In view of preventing the leakage of the bodily waste, the notch 110 is preferably narrower than the width of the lower-back stretch unit 85.

Furthermore, if the absorber 40 is contracted in the product widthwise direction W by the lower-back stretch unit 85 and the space between the absorbers at both sides in the product widthwise direction from the notch 110 also narrows, the part towards the end of the side of the rear waistline region 30 of the notch 110 shifts more towards the center in the product widthwise direction W than the part towards the crotch region 25, and therefore, a difference in the amount of contraction in the product widthwise direction W occurs between the part at the side of the rear waistline region 30 and the part towards the crotch region 25, because of which the rear waistline region 30 rises.

That is, because the lower-back stretch unit 85 that can expand and contract in the product widthwise direction W, and the wedge-shaped notch 110 are present, the disposable diaper 10 easily swells at the non-skin surface side resulting in a cup shape, when the disposable diaper 10 is worn. Additionally, because the first region 41 is arranged at the side of the crotch region 25 beyond the lower-back stretch unit 85, a curved portion extending in the product widthwise direction W of the disposable diaper 10 is formed in the boundary portion between the contracted region and the un-contracted region, and when the inner side in the product longitudinal direction from the notch 110 is taken as the reference surface, the rear waistline region 30 deforms into a state where it rises further up than the reference surface. Therefore, the disposable diaper 10 itself deforms so as to run along the curve in the back and the hips of the wearer, which makes it difficult to generate a space between the disposable diaper and the body of the wearer, also making it difficult to generate a shift or a space around the lower back at the dorsal side. In other words, according to the disposable diaper 10, because an element that forms a cup shape in the product widthwise direction W, and an element that forms a cup shape in the product longitudinal direction L are both provided, it is easy to run along the body of the wearer who often adopts a C-shaped curved posture.

Furthermore, in the present embodiment, because the absorbent core 40a does not exist in the notch 110, and the lower-back stretch unit 85 exists so as to overlap the notch 110, the part towards the end of the side of the rear waistline region 30 in the product longitudinal direction L shifts more towards the center in the product widthwise direction W than the position of the end of the absorbent core 40*a* because of which the rise of the rear waistline region 30 becomes more remarkable, and the above-mentioned cup shape can be formed in a more stable manner.

In the present embodiment, because the lower-back stretch unit 85 exists beyond the side edges in the product widthwise direction W of the absorbent core 40*a*, the disposable diaper 10 can be formed in the shape of a cup, and the absorbent core 40*a* positioned towards the end of the side of the rear waistline region 30 in the product longitudinal direction L can actively run along the body of the wearer. Furthermore, because at least a part of the lower-back stretch unit 85 and the low rigidity region exists in a tape arrangement region A1 provided with a pair of fastening tapes 90, even when the disposable diaper 10 is worn with spreading the disposable diaper 10 and then making the wearer lie down on the disposable diaper, the lower-back stretch unit 85 that exists beyond the side edges in the product widthwise direction W of the absorbent core 40*a* is not placed under the body of the wearer, and as a result, by pulling the fastening tapes 90, the side edges of the lower-back stretch unit 85 expand, and the disposable diaper can be more surely made to run the cup-shaped position towards the waist along the body of the wearer.

In the present embodiment, the absorbent core 40*a* at the outer side in the product widthwise direction from the notch 110 has a convex shape towards the side of the rear waistline region. Therefore, in addition to the above-mentioned fact that a cup shape in which the disposable diaper 10 swells at the non-skin surface side can be formed easily, the surface area of the absorbent core 40*a* is maintained, enabling the prevention of leakage of bodily waste from the ends of the absorbent core 40*a*.

In the present embodiment, the notch 110 is wedge shaped, and the boundary between the absorbent core 40*a* and the notch 110 is in the shape of an arch such as a convex shape towards the crotch region 25. The radius of the arc is between 50 mm and 200 mm. Therefore, the width in the product widthwise direction W of the notch 110 increases non-linearly towards the end of the side of the rear waistline region 30 in the product longitudinal direction L, because of which the rise of the rear waistline region 30 becomes more remarkable, and the cup shape can easily be formed in a more stable manner. Additionally, because the boundary between the absorbent core 40*a* and the notch 110 is formed in the shape of an arc such as a convex shape towards the crotch region 25, due to the contraction of the notch 110, the rear waistline region 30 takes a curved cup shape, which can easily run along the curved hips of the wearer.

Furthermore, due to the formation of the notch 110, a convex shape towards the side of the rear waistline region is formed on both left and right at the end of the side of the rear waistline region of the absorber 40. The shape of the absorber is in retrospect of placing the hips, and is effective in more easily enabling the user to set the diaper at the correct position for the wearer.

The boundary between the first region 41 and the second region 42 is arranged along the product widthwise direction W. A boundary line BL12 that virtually illustrates the boundary between the first region 41 and the second region 42 is shown in FIG. 4.

The boundary between the first region 41 and the second region 42 is arranged at the side of the crotch region from an end 75R (see FIG. 2) at the side of the rear waistline region of the leg stretch unit 75, and from an end 84R (see FIG. 2) at the side of the rear waistline region of the contracted unit 84 in the leg side gathers 80. Furthermore, an end 41R at the side of the rear waistline region of the first region 41 is arranged at the side of the rear waistline region from the end 75R at the side of the rear waistline region of the leg stretch unit 75, and the end 84R at the side of the rear waistline region of the contracted unit 84. It must be noted that the end 41R at the side of the rear waistline region of the first region 41 is the end 40R at the side of the rear waistline region of the absorber 40.

That is, the end 75R at the side of the rear waistline region of the leg stretch unit, and the end 84R at the side of the rear waistline region of the contracted unit in the leg side gathers are arranged so as to overlap the first region 41 in the product longitudinal direction.

When the so-called open-type disposable diaper is put on new-borns or the like, the disposable diaper is worn by placing the hips of the wearer in the rear waistline region of the absorber, with the disposable diaper in an expanded state in the longitudinal direction. The disposable diaper is stretched in the product longitudinal direction by the leg stretch unit 75 and the leg side gathers 80, and the absorber 40 stretches in the product longitudinal direction. In this way, if the absorber 40 contracts in the product longitudinal direction, wrinkles occur particularly in the region in which the end in the product longitudinal direction of the leg stretch unit 75 and the end in the product longitudinal direction of the leg side stretch unit are arranged, and also in a fixed range extending from this region towards the widthwise direction, because of which the hips cannot be placed at the correct position causing the wearing position to deviate. Particularly, in the region close to the end 75R at the side of the rear waistline region of the leg stretch unit 75, and the end 84R at the side of the rear waistline region of the contracted unit 84 of the leg side gathers 80, the absorber, etc. is easily contracted in a remarkable manner by both the stretch units.

However, the end 75R at the side of the rear waistline region of the leg stretch unit 75, and the end 84R at the side of the rear waistline region of the contracted unit 84 of the leg side gathers 80 are positioned in the region in which the first region having a relatively higher rigidity is arranged in the product longitudinal direction. Therefore, the stretching of the absorber by the end 75R at the side of the rear waistline region of the leg stretch unit 75, and the end 84R at the side of the rear waistline region of the contracted unit 84 of the leg side gathers 80 can be prevented by the first region having a relatively higher rigidity. Therefore, when the disposable diaper is worn, the wearer can be placed at the correct position, and the deviation in the wearing position can be prevented.

The joining portion 81 arranged at the side of the rear waistline region from the contracted unit 84 is provided in the leg side gathers 80 of the rear waistline region 30. The end at the side of the front waistline region of the joining portion 81 is arranged at the side of the front waistline region from the end 41R at the side of the rear waistline region of the first region, and is also arranged at the side of the rear waistline region from an end 41F at the side of the front waistline region of the first region. That is, the end at the side of the front waistline region of the joining portion 81 arranged at the side of the rear waistline region from the contracted unit 84 is arranged at the side of the skin contact surface of the first region 41, and overlaps the first region 41 in the plan view.

The end at the side of the front waistline region of the joining portion 81 arranged at the side of the rear waistline region from the contracted unit 84 is the portion in which the leg side gathers rise from the side of the topsheet 50, and is also the portion that easily becomes the inflection point of the deformation of the absorber. Because the joining portion 81 overlaps the first region, the deformation of the absorber can be prevented effectively by the first region having a relatively higher rigidity.

Furthermore, the end 41R at the side of the rear waistline region of the first region 41 is arranged at the side of the front waistline region from an end 10R at the side of the rear waistline region of the disposable diaper. For example, if the first region is arranged at the back end of the disposable diaper, the end 41R at the side of the rear waistline region of the first region having a relatively higher rigidity comes in contact with the skin when the disposable diaper is worn, and can stimulate the skin. However, as the first region is positioned in front of the end 10R at the side of the rear waistline region of the disposable diaper, it becomes difficult for the first region to come in direct contact with the skin, and thus the stimulation and feeling of discomfort can be reduced.

In addition, the first region 41 is provided between the pair of fastening tapes 90 in the product widthwise direction. When the disposable diaper is worn, the fastening tape is secured to the front waistline region, and a certain region extending from the fastening tape in the widthwise direction is held onto the lower back of the wearer. If wrinkles or waviness occur in the certain region extending from the fastening tape in the widthwise direction, a deviation in the position of the diaper can occur easily when the disposable diaper is worn. However, by providing the first region having a relatively higher rigidity between the fastening tapes, the waviness and wrinkles in the absorber can be controlled and a deviation in the position of the diaper when the disposable diaper is worn can be prevented.

Furthermore, the absorbent core 40a of the absorber has a constricted region 46 in which the length in the product widthwise direction of the crotch region is shorter than the length in the product widthwise direction of the front waistline region and the rear waistline region. The boundary between the first region and the second region 42 which is the end 41F at the side of the front waistline region of the first region 41 is arranged at the side of the rear waistline region from the constricted region 46 of the absorber. Therefore, the second region 42 having a relatively lower rigidity is arranged in the constricted region 46.

The hips of the wearer are curved and bulging. The absorber of the disposable diaper that is in contact with the hips is configured to expand from the inner side in the widthwise direction to the outer side in the widthwise direction, from the crotch region 25 towards the rear waistline region, and the absorber is arranged such that the expanded portion runs along the hips to cover the hips. On the other hand, the lower back portion that is positioned above the hips of the wearer is a flat portion with a lesser bulge as compared to the hips. The absorber of the disposable diaper that is in contact with the hips has a higher bending rigidity and is configured to be able to run flatly along the body.

Because the boundary between the first region 41 and the second region 42 is arranged at the side of the rear waistline region from the constricted region 46, the second region having a relatively lower rigidity is arranged therein, and the absorber is arranged along the curved hips. On the other hand, in the portion that is in contact with the lower back at the side of the rear waistline region from the constricted region, the first region having a relatively higher rigidity is arranged, and the absorber is arranged to run flatly along the body.

The end 41F at the side of the front waistline region of the first region is arranged at the side of the rear waistline region from the crotch stretch unit 200a. As described above, the crotch region 25 is pulled up to the side of the wearer by the crotch stretch unit 200a that contracts at least in the product longitudinal direction. Thus, the crotch unit 200 is arranged at a position close to the wearer. Therefore, even when a weight or load is exerted from the outside, the absorber 40 is easily arranged along a position that is close to the body.

Furthermore, the crotch stretch unit 200a is contracted in at least the product longitudinal direction, which has high rigidity as compared to the surrounding portion that is not contracted. Thus, the boundary between the crotch stretch unit 200a and the surrounding becomes an inflection point due to the rigidity difference. A leg stretch unit 75 and/or leg side gathers 80 are present in the product longitudinal direction beyond the end at the side of the front waistline region of the crotch stretch unit 200a and the end at the side of the rear waistline region. Therefore, an inflection point is provided at both ends in the longitudinal direction of the crotch stretch unit 200a, and the crotch stretch unit is deformed to become the bottom unit.

The crotch stretch unit 200a positioned in the crotch region 25 configures the bottom unit, and can be arranged opposite the crotch of the wearer. In addition, the side of the front waistline region and the side of the rear waistline region from the crotch stretch unit have a lower rigidity than the crotch stretch unit, and can be arranged along the ventral and dorsal sides of the wearer.

Because the crotch stretch unit is provided at the side of the front waistline region from the first region, when the disposable diaper is expanded in the longitudinal direction, contraction occurs due to the crotch stretch unit, and the deformation of the absorber can be absorbed. By deforming the absorber in the crotch region, it becomes easy to maintain the first region 41 of the rear waistline region in a relatively smooth state. Thus, the rear waistline region of the absorber is maintained in a smooth state when the disposable diaper is worn, which makes it possible to wear the disposable diaper at the correct position.

(4) Method of Wearing Disposable Diaper

Figure 5:
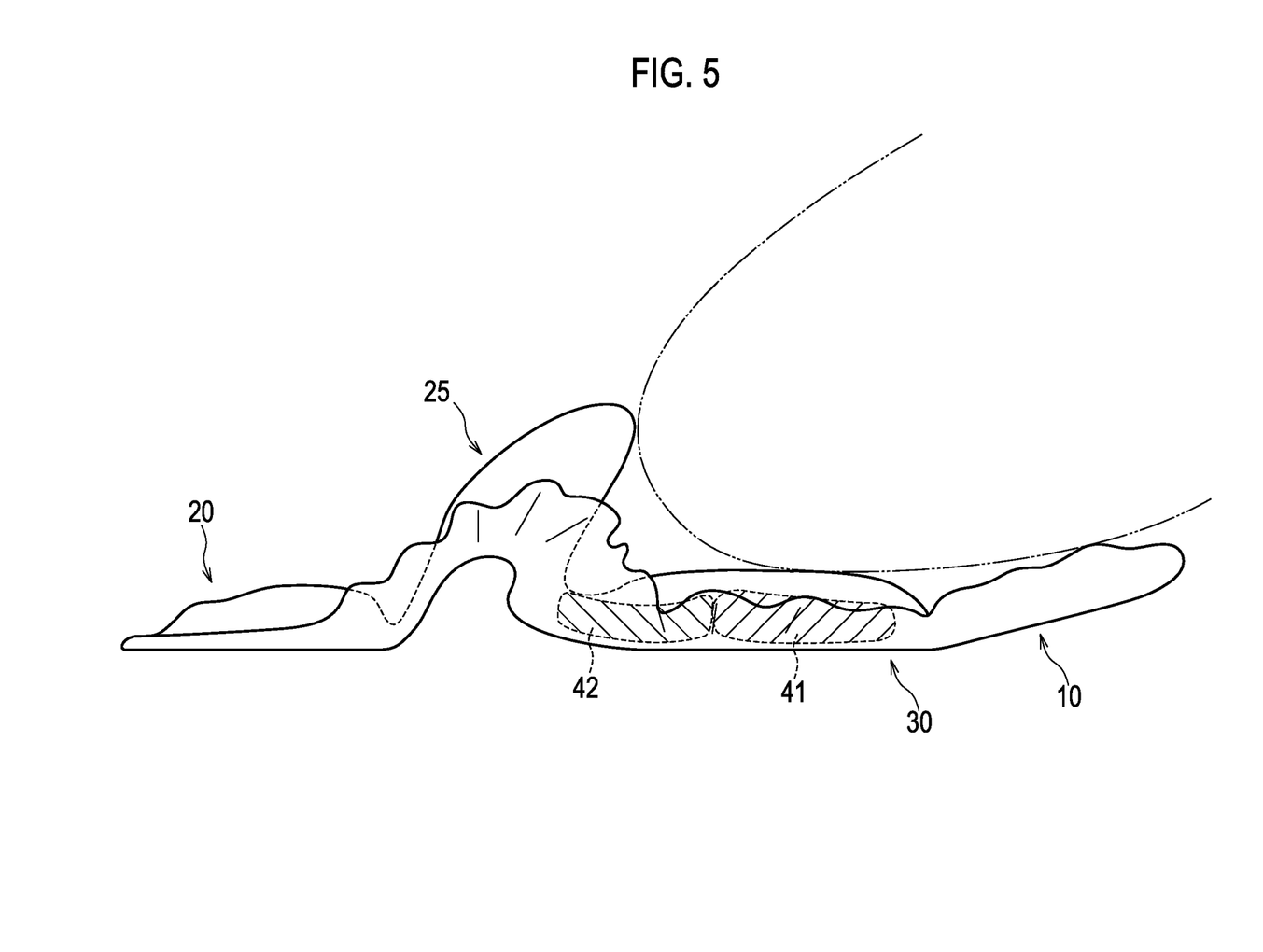
FIG. 5 is a diagram illustrating a state in which the disposable diaper according to the present embodiment is worn by the wearer.
Figure 6:
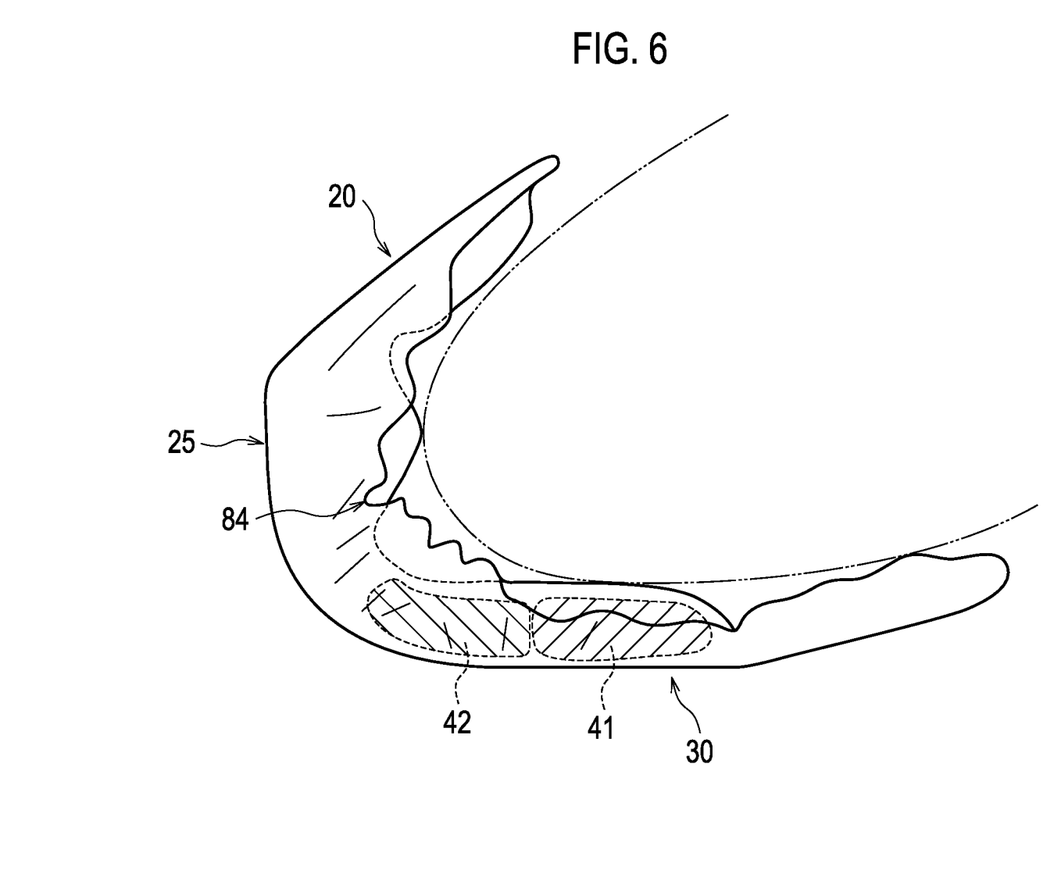
FIG. 6 is a diagram illustrating a state in which the disposable diaper according to the present embodiment is worn by the wearer.
Figure 7:
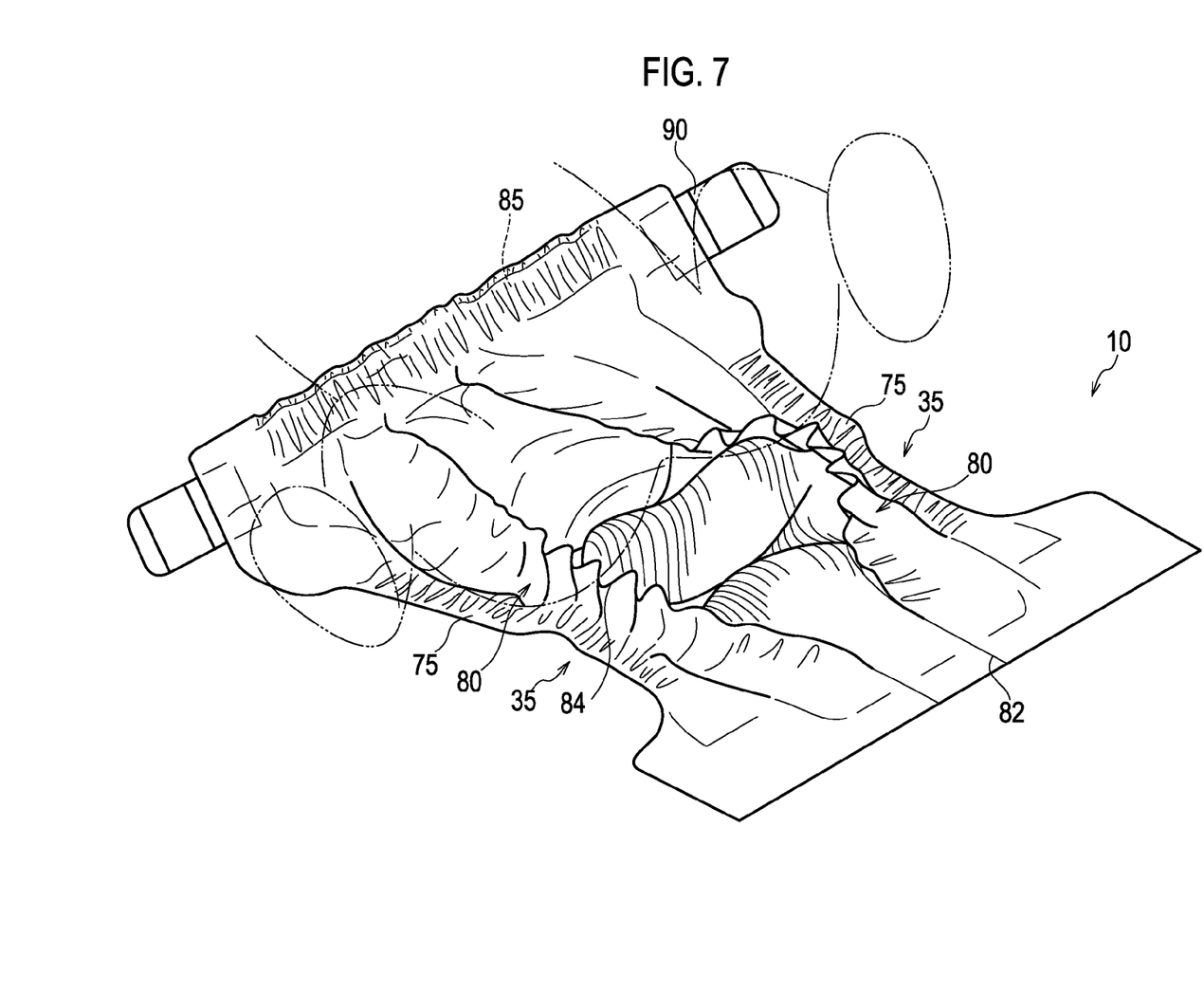
FIG. 7 is a diagram illustrating a state in which the disposable diaper according to the present embodiment is worn by the wearer.

Next, with reference to FIG. 5 through FIG. 7, the method in which the disposable diaper 10 is put on the wearer is explained. For illustration purposes, in FIG. 5 through FIG. 7, the first region 41 and the second region 42 of the absorber arranged at the inner side of the disposable diaper have been shown schematically.

Firstly, when the disposable diaper 10 is expanded, then as illustrated in FIG. 5 and FIG. 7, in the natural state, the crotch stretch unit 200a contracts, and the crotch region 25 rises with the end at the side of the rear waistline region 30 of the crotch stretch unit 200a and the end at the side of the front waistline region 20 of the crotch stretch unit 200a as the base point.

The leg stretch unit 75 and the leg side gathers 80 contract, and a force is exerted on the entire disposable diaper so as to contract in the product longitudinal direction. However, the region in which the absorber 40 of the disposable diaper is arranged has a high rigidity as compared to the region in which the absorber is not arranged, which makes it difficult to contract. Thus, the absorber-arranged region in which the absorber is arranged is easily set to a smooth state.

In addition, the first region 41 of the absorber is configured to have the highest rigidity in the absorber-arranged region. Thus, it becomes easy to main a particularly smooth state. The first region 41 includes the end of the side of the rear waistline region of the absorber 40, and is the region that is in contact with the hips of the wearer. Thus, as illustrated in FIG. 5 and FIG. 7, the hips of the wearer can be placed on the absorber that is maintained in a smooth state, and the wearer can be made to lie down on the disposable diaper.

Secondly, after making the wearer lie down on the expanded disposable diaper 10 in the natural state, as illustrated in FIG. 6, by folding back the front waistline region 20 and installing the front waistline region 20 and the rear waistline region 30 with the fastening tape 90, the disposable diaper 10 is put on the body of the wearer.

The second region at the side of the front waistline region from the first region that is in contact with the hips has a lower rigidity than the first region 41, and is deformed more easily than the first region. Thus, the second region can be arranged along the ventral side of the wearer.

(5) Operation and Effect

The end 75R at the side of the rear waistline region of the leg stretch unit 75, and the end 84R at the side of the rear waistline region of the contracted unit 84 of the leg side gathers 80 are positioned in the region in which the first region having a relatively higher rigidity is arranged in the product longitudinal direction. Therefore, the stretching of the absorber by the end 75R at the side of the rear waistline region of the leg stretch unit 75, and the end 84R at the side of the rear waistline region of the contracted unit 84 of the leg side gathers 80 can be prevented by the first region having a relatively higher rigidity. Therefore, when the disposable diaper is worn, the wearer can be placed at the correct position, and the deviation in the wearing position can be prevented.

Furthermore, a plurality of compressed units of the disposable diaper 10 are formed intermittently across the entire first region. Thus, the rigidity of the entire first region can be increased in an almost uniform manner. Also, because a plurality of compressed units are arranged intermittently in the first region, compressed portions and uncompressed portions co-exist in the first region. The uncompressed portions have a lower rigidity than the compressed portions and can be deformed flexibly, because of which the rigidity of the first region 41 can be increased, and the first region 41 can be arranged along the line of the body having a roundness.

Furthermore, because the crotch stretch unit 200a is provided in the absorber, the end in the product longitudinal direction of the crotch stretch unit 200a becomes the inflection point, which makes the deformation of the absorber easier. Furthermore, a low rigidity unit is formed at the inner side in the product longitudinal direction from the crotch stretch unit, and the absorbent core 40a positioned more towards the front waistline region 20 than the low rigidity unit, as well as the absorbent core 40a positioned more towards the rear waistline region 30 than the low rigidity unit rise from the "bottom unit", and curve easily to run along the roundness of the body of the wearer (abdomen and hips), because of which the shape of the disposable diaper can be brought closer to the body of the wearer.

In addition, according to the disposable diaper 10 of the present embodiment, when the disposable diaper 10 is expanded, then in the natural state and while maintaining the first region that is in contact with the hips of the wearer in a smooth state, the crotch region 25 can be made to rise with the end in the product longitudinal direction of the crotch stretch unit 200a as the base point.

By arranging the crotch portion of the wearer in the risen crotch region 25, and by bringing the hips of the wearer in contact with a part of the rear waistline region 30, the person who assists a wearer in wearing can exactly put the disposable diaper 10 on the wearer. Thus, the induction of leakage due to a deviation in the wearing position of the disposable diaper 10 can be avoided.

(6) Other Embodiments

As described above, the present invention is disclosed through the above embodiments of the present invention. However, it should not be interpreted that the statements and drawings constituting a part of the present disclosure limit the present invention. From this disclosure, a variety of alternate embodiments, examples, and applicable techniques will become apparent to one skilled in the art.

For example, a compressed unit is formed in the absorber at the inner side in the product longitudinal direction from the second region, and a high rigidity region having a rigidity that is higher than the second region may be provided. That is, as for the absorber according to the present invention, the second region having a lower rigidity than the first region may be provided at least at the inner side in the product longitudinal direction from the first region having a high rigidity, and a high rigidity region having a rigidity that is same as or higher than the rigidity of the first region may be provided at the inner side in the product longitudinal direction from the second region.

Furthermore, in the disposable diaper according to the modification, rather than leg gathers formed from an elastic nonwoven sheet, leg gathers formed from thread-like elastic members may be provided.

As described above, it is of course that the present invention includes various embodiments and the like not described here. Therefore, the technical range of the present invention is to be defined only by the inventive specific matter according to the adequate claims from the above description.

The entire contents of Japanese Patent Application No. 2012-082909 (filed on Mar. 30, 2012) are incorporated in the present specification by reference.

INDUSTRIAL APPLICABILITY

It is possible to provide an absorbent article, with which it is possible to easily wear an open-type disposable diaper having a fastening tape at the correct position, and to prevent the deviation of the wearing position.

REFERENCE SIGNS LIST

10 . . . disposable diaper
20 . . . Front waistline region
25 . . . Crotch region
30 . . . Rear waistline region
35 . . . Leg hole opening
40 . . . Absorber
40a . . . Absorbent core
40b . . . Core wrap 41 . . . First region
42 . . . Second region
45 . . . Compressed unit
46 . . . Constricted region
50 . . . Topsheet
60 . . . Exterior sheet
60a . . . backsheet
70 . . . Side flap
71 . . . Elastic member
75 . . . Leg stretch unit
80 . . . Leg side gather
81 . . . Joining portion
82 . . . Free end portion
84 . . . Contracted unit
90 . . . Fastening tape
115 . . . Notch
125 . . . Notch
200 . . . Crotch unit
200a . . . Crotch stretch unit
BL12 . . . Boundary line between the first region and the second region
L . . . Product longitudinal direction
W . . . Product widthwise direction

The invention claimed is:

1. A disposable diaper, comprising:
a front waistline region;
a rear waistline region;
a crotch region positioned between the front waistline region and the rear waistline region;
an absorber running across the crotch region and extending in the front waistline region and the rear waistline region;
a product longitudinal direction from the front waistline region towards the rear waistline region;
a product widthwise direction perpendicular to the product longitudinal direction;
a pair of fastening tapes extending outwardly from the rear waistline region in the product widthwise direction, and being secured to the front waistline region;
a pair of leg hole openings;
a pair of leg stretch units each arranged around one of the leg hole openings and configured to expand and contract along at least the product longitudinal direction; and
a pair of leg side stretch units arranged in the product widthwise direction between the leg stretch units, and each of the leg side stretch units having a contracted unit configured to expand and contract along the product longitudinal direction,
wherein
the absorber includes
a first region extending from an end of the absorber at a side of the rear waistline region towards a side of the crotch region, and
a second region arranged adjacent to the first region at the side of the crotch region, and having a lower bending rigidity than the first region,
the first region has a rear end at the side of the rear waistline region and a front end at the side of the crotch region,
ends of the leg stretch units at the side of the rear waistline region and ends of the contracted units at the side of the rear waistline region are arranged between the rear end of the first region and the front end of the first region in the product longitudinal direction, and
the absorber has a plurality of compressed units arranged intermittently in the first region to increase the bending rigidity of the first region to be higher than the bending rigidity of the second region.

2. The disposable diaper according to claim 1, wherein the plurality of compressed units where the absorber is compressed in a product thickness direction is arranged in the first region, the product thickness direction crossing the product longitudinal direction and the product widthwise direction.

3. The disposable diaper according to claim 2, wherein the plurality of the compressed units are formed intermittently across an entirety of the first region.

4. The disposable diaper according to claim 1, further comprising:
a liquid-permeable topsheet arranged at a skin contact surface side of the absorber; and
a liquid-impermeable backsheet arranged at a non-skin contact surface side of the absorber,
wherein
each of the leg side stretch units has a joining portion arranged at an outer side of the contracted unit in the product longitudinal direction, and joining the leg side stretch unit either to the topsheet or the backsheet,
the joining portion is arranged at the side of the rear waistline region, and
an end of the joining portion at the side of the crotch region is arranged between the rear end of the first region and the front end of the first region in the product longitudinal direction.

5. The disposable diaper according to claim 1, wherein the rear end of the first region is arranged forward of an end of the disposable diaper at the rear waistline region in the product longitudinal direction.

6. The disposable diaper according to claim 1, wherein the first region is between the pair of fastening tapes in the product widthwise direction.

7. The disposable diaper according to claim 1, further comprising a crotch stretch unit in the crotch region, wherein
the crotch stretch unit is in an absorber-arranged region in which the absorber is arranged, and configured to expand and contract in the product longitudinal direction, and
the front end of the first region is arranged rearward of the crotch stretch unit in the product longitudinal direction.

8. The disposable diaper according to claim 1, wherein
the absorber further has a low rigidity region that either has a basis weight lower than other parts of the absorber, or where an absorbent core does not exist,
the end of the absorber at the side of the rear waistline region has a center in the product widthwise direction, and
the low rigidity region extends from the center of the end of the absorber towards the front end of the first region.

9. The disposable diaper according to claim 8, wherein a width of the low rigidity region in the product widthwise direction is reduced towards the side of the crotch region from the side of the rear waistline region.

10. The disposable diaper according to claim 8, further comprising a lower-back stretch unit configured to expand and contract in at least the product widthwise direction, wherein
the lower-back stretch unit is at the rear waistline region and between the pair of fastening tapes in the product widthwise direction, and
at least a part of the low rigidity region is overlapping the lower-back stretch unit in a plan view.

11. The disposable diaper according to claim 3, wherein the entirety of the first region extends all the way across the absorber in the product widthwise direction.

12. The disposable diaper according to claim 1, wherein the ends of the contracted units at the side of the rear waistline region overlap the plurality of compressed units in a plan view of the disposable diaper.

13. The disposable diaper according to claim 1, wherein the end of the absorber at the side of the rear waistline region coincides with the rear end of the first region.

14. The disposable diaper according to claim 7, wherein
the crotch stretch unit includes a stretchable sheet or elastic members, and
an entirety of the crotch stretch unit is positioned forward of the plurality of compressed units in the product longitudinal direction.

\* \* \* \* \*